United States Patent
Bailly et al.

(10) Patent No.: US 9,271,704 B2
(45) Date of Patent: Mar. 1, 2016

(54) REEL FOR SURGICAL TAPE

(75) Inventors: Pierre Bailly, Caluire (FR); Karine Trogneux, Villeurbanne (FR); Jacques Tostain, L'Etrat (FR)

(73) Assignee: Sofradim Production (FR)

( * ) Notice: Subject to any disclaimer, the term of this patent is extended or adjusted under 35 U.S.C. 154(b) by 699 days.

(21) Appl. No.: 12/671,380

(22) PCT Filed: Jul. 31, 2008

(86) PCT No.: PCT/IB2008/002889
§ 371 (c)(1),
(2), (4) Date: May 5, 2010

(87) PCT Pub. No.: WO2009/016517
PCT Pub. Date: Feb. 5, 2009

(65) Prior Publication Data
US 2010/0262164 A1 Oct. 14, 2010

Related U.S. Application Data

(60) Provisional application No. 60/962,703, filed on Jul. 31, 2007.

(30) Foreign Application Priority Data

Jul. 31, 2007 (FR) ...................................... 07/05591

(51) Int. Cl.
*A61F 2/00* (2006.01)
*A61B 17/00* (2006.01)
(Continued)

(52) U.S. Cl.
CPC ....... *A61B 17/00234* (2013.01); *A61B 17/0483* (2013.01); *A61B 17/068* (2013.01);
(Continued)

(58) Field of Classification Search
CPC ............. A61B 17/0483; A61B 17/068; A61B 2017/00805; A61B 2017/0409; A61B 2017/06052; A61B 17/06109; A61F 2/0045
USPC ........................ 600/30, 29, 37; 128/897–899; 606/139–142, 144, 148, 219, 143
See application file for complete search history.

(56) References Cited

U.S. PATENT DOCUMENTS 4,741,330 A * 5/1988 Hayhurst ....................... 606/144
5,439,467 A 8/1995 Benderev et al.
(Continued)

FOREIGN PATENT DOCUMENTS

WO WO 01/93656 12/2001
WO WO 02/02031 1/2002
(Continued)

OTHER PUBLICATIONS

International Search Report from International Application No. PCT/IB2008/002889 mailed Mar. 17, 2009.

*Primary Examiner* — Catherine B Kuhlman
*Assistant Examiner* — Shannon McBride

(57) ABSTRACT

The present invention relates to a component (101) intended to be mounted on the ejection barrel of a device for dispensing surgical staples, characterized in that it comprises: fixing means (102) designed to fix said component (101) on said ejection barrel removably or non-removably, securing means (103) for securing a surgical tape to said component (101), said securing means allowing said tape to slide within said component (101). The invention further relates to a kit comprising such a component and/or a device for dispensing surgical staples and/or a surgical tape.

12 Claims, 8 Drawing Sheets

Figure 1:
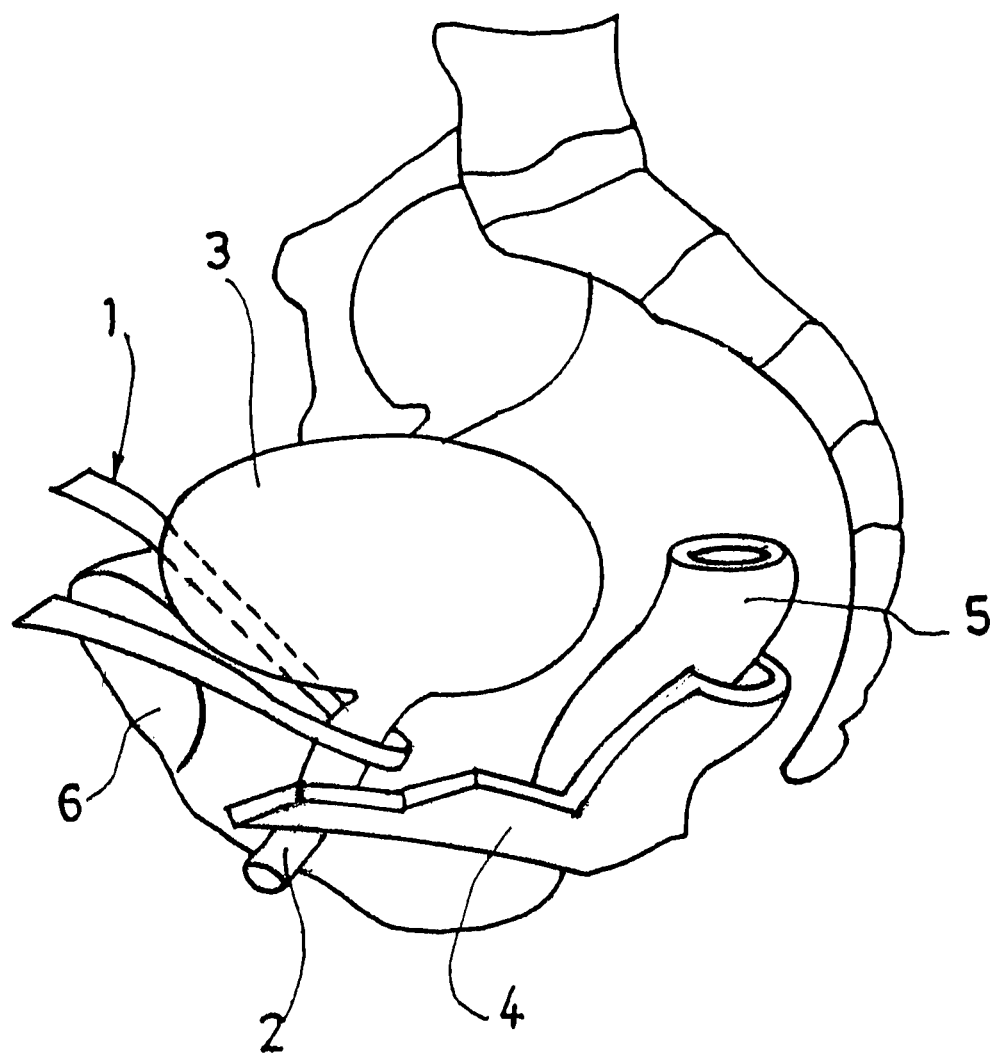

(51) Int. Cl.
*A61B 17/04* (2006.01)
*A61B 17/068* (2006.01)
*A61B 17/06* (2006.01)

(52) U.S. Cl.
CPC .............. *A61B2017/00805* (2013.01); *A61B 2017/0409* (2013.01); *A61B 2017/06052* (2013.01); *A61F 2/0045* (2013.01)

(56) References Cited

U.S. PATENT DOCUMENTS

| | | | |
|---|---|---|---|
| 5,873,891 A | | 2/1999 | Sohn |
| 6,053,935 A | * | 4/2000 | Brenneman et al. .......... 606/232 |
| 6,245,082 B1 | * | 6/2001 | Gellman et al. .............. 606/151 |
| 6,494,887 B1 | * | 12/2002 | Kaladelfos ................... 606/148 |
| 2002/0095064 A1 | * | 7/2002 | Beyar .............................. 600/30 |
| 2003/0135225 A1 | | 7/2003 | Harari et al. |
| 2006/0058575 A1 | * | 3/2006 | Zaddem et al. ................ 600/30 |
| 2006/0063968 A1 | * | 3/2006 | Anderson et al. .............. 600/30 |
| 2006/0229493 A1 | * | 10/2006 | Weiser et al. .................. 600/37 |
| 2008/0078808 A1 | * | 4/2008 | Hess et al. ................. 227/181.1 |

FOREIGN PATENT DOCUMENTS

| | | |
|---|---|---|
| WO | WO 03/075773 | 9/2003 |
| WO | WO 03/086205 | 10/2003 |
| WO | Wo 2005/004727 | 1/2005 |
| WO | WO 2005/067802 | 7/2005 |
| WO | WO 2006/005117 | 1/2006 |
| WO | WO 2006/037893 | 4/2006 |

\* cited by examiner

REEL FOR SURGICAL TAPE

CROSS-REFERENCE TO RELATED APPLICATIONS

This application is a U.S. National Stage Application filed under 35 U.S.C. §371(a) of International Application No. PCT/IB2008/002889, which claims the benefit of and priority to U.S. Provisional Application No. 60/962,703, filed on Jul. 31, 2007 and French Application 07/05591 filed Jul. 31, 2007.

The present invention relates to a component, for example a reel, intended to be mounted on the ejection barrel of a device for dispensing surgical staples, for the purpose of unreeling a surgical tape at the moment of its implantation in the human body. The present invention further relates to a kit that comprises such a component and/or a device for dispensing surgical staples and/or a surgical tape.

The component and/or kits according to the invention are particularly useful in the treatment of female stress urinary incontinence, but they can be used for implanting any type of surgical tape that needs to be fixed in the tissues at one or more locations, particularly at at least two locations.

The problems of stress urinary incontinence are generally treated by performing a surgical intervention involving implantation of a tape, which forms a support for the urethra and for this reason is commonly called a suburethral tape. These suburethral tapes generally have an elongate rectangular shape.

A first type of access route for implanting these tapes involves the ascending, descending or mixed retropubic routes. The tape is fastened at each of its ends to two puncture needles that allow it to be passed through the tissues. In the ascending route, the two needles are introduced into the tissues through a vaginal incision below the urethra, ascend on both sides of the urethra and of the bladder, then pass through the abdomen behind the pubic symphysis and emerge from the abdomen by penetrating through the skin above the pubis. The tape follows the same path and anchors itself naturally or is fixed with the aid of sutures or staples in the abdominal wall. In the descending route, the needles and the tape follow the opposite path, starting from abdominal incisions above the pubis and ending in the vaginal incision. In the mixed route, the tape follows a descending path on one side and an ascending path on the other side.

FIG. 1 shows a simplified perspective view of a woman's pelvis, depicting a suburethral tape 1 fitted in place by a retropubic route as described above, the urethra 2, the bladder 3, part of the left levator muscle 4, the rectum 5, and part of the os pubis 6. The tape 1 is indicated by broken lines when hidden by the bladder 3 in the figure. As will be evident from the preceding paragraph and from said FIG. 1, the path followed by the tape 1 has to loop round the urethra 2, pass close to the bladder 3 twice, then extend along the os pubis 6. This retropubic and prevesical path is a long one. Furthermore, this surgical technique demands systematic monitoring by endoscopy during the positioning of the tape, for example by cystoscopy, particularly in view of the risks of perforation of the bladder. This method also entails risks of perforation of the intestines and vessels.

A second type of access route involves ones called "transobturator" routes, in which the tape passes through the right and left obturator muscles, via the right and left obturator foramens of the iliac bone, from the inside outwards or from the outside inwards. These routes are also called "lateral routes". This technique is described in the application WO02/02031. For example, an Emmet needle is introduced through an incision made in the thigh, in line with the right obturator foramen, and then exits through a vaginal incision. A second Emmet needle is introduced through an incision made in the thigh, in line with the left obturator foramen, and exits via the same vaginal incision. The tape is then connected with its two ends to the two needles and it is pulled, on both sides of the urethra, by the return of each of the needles through the muscle thickness of the internal and external obturator muscles, then the adductor muscles of the thigh, as far as the surface of the skin.

Figure 2:
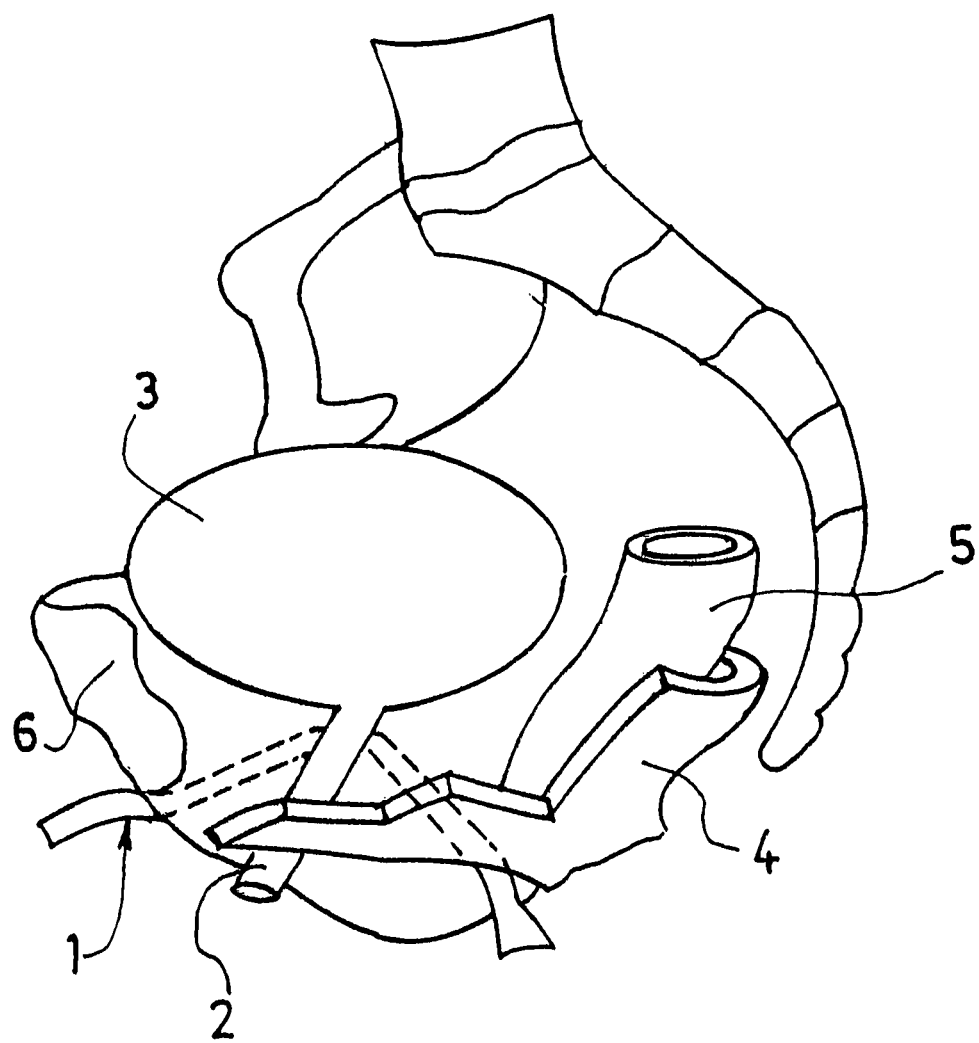

FIG. 2 shows a simplified perspective view, similar to FIG. 1, in which the suburethral tape 1 has been fitted in place by a transobturator access route. As will be seen from this figure, the tape 1 does not pass near the vessel 3, as it does in the retropubic access route. However, the horizontal placement of the tape 1 in the transobturator access route may in some cases be responsible for a pulling effect on the wall of the vagina (not shown), which generates dyspareunia. The placement does not totally exclude the risk of injury to the vagina or urethra. Moreover, with this method, if an infection occurs along the length of the tape, the sequelae are serious and difficult to treat, with a risk of cellulitis of the thigh and pelvis.

It therefore appears that the retropubic and transobturator access routes have disadvantages, due in particular to the length and nature of the paths followed by the needles and the tapes that are used for suspension of the urethra.

Attempts have therefore been made to develop devices which can be used for treating female stress urinary incontinence and which, although providing effective support of the urethra, cause minimal trauma to the surrounding tissues. In particular, attempts have been made to make available a device which could be fitted in place without the need to perform an excessive vaginal dissection and without having to make incisions in the abdomen or lateral incisions (thigh muscles).

Figure 3:
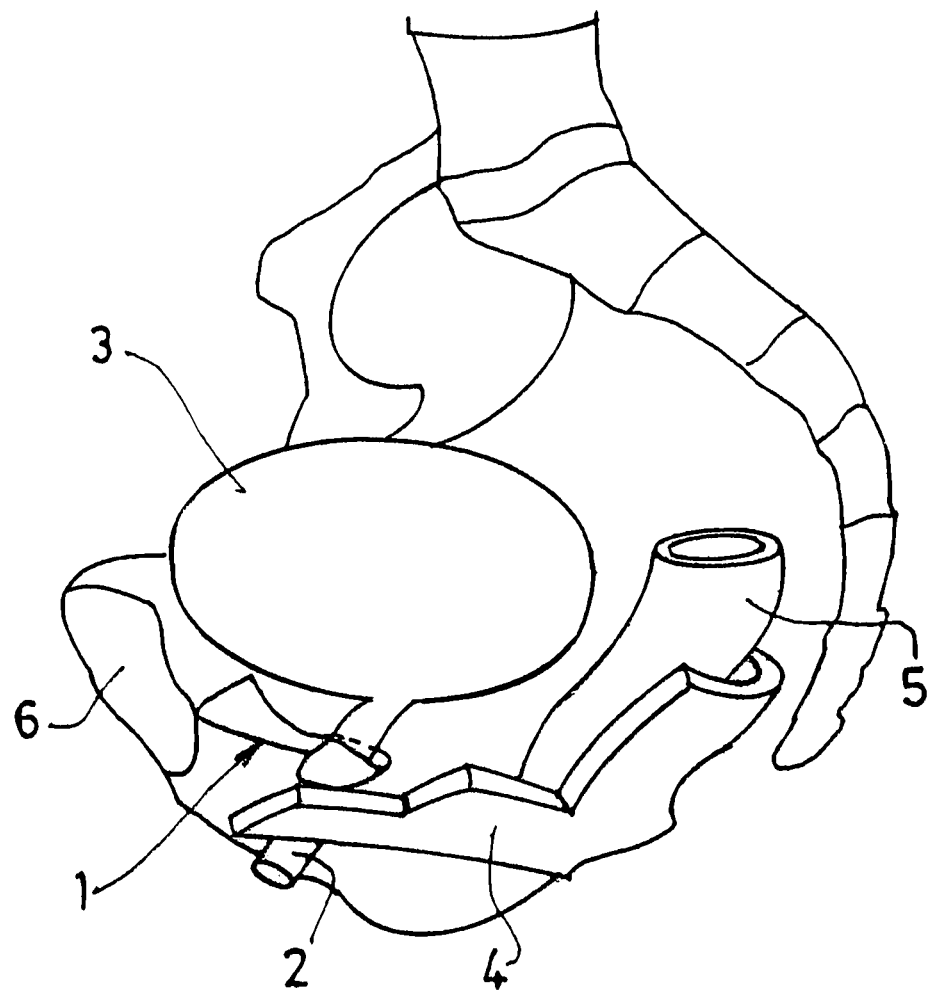

Document WO03/086205 describes such a surgical device which is used for treating female stress urinary incontinence and with which the tape follows a short path that causes very little trauma. In such a case, as shown in FIG. 3, the device comprises a tape 1 which is made of flexible biocompatible material of generally rectangular and elongate shape and is dimensioned to extend from the anterior attachment of the right levator muscle 4, or left levator muscle (not shown), in the area of the paravesical fossa, to the anterior attachment of the left levator muscle, or right levator muscle 4, in the area of the paravesical fossa, passing under the urethra 2.

Such a tape is shorter than a tape intended to be implanted by the retropubic and transobturator access routes, and the path that it follows inside the woman's abdomen is particularly short. Indeed, such a tape does not exit through abdominal incisions, and it therefore does not pass through the abdominal tissues. Nor is it necessary to use needles that pass through these tissues in order to fit the device according to the invention in place.

However, because of its relatively short form, such a tape is in contact with the walls of the tissues over a smaller surface area and its adherence, through development of fibrosis around and within the prosthesis after cell recolonization, may not be sufficient in the first few days following the implantation.

Devices for attaching a tape at two different points of an implantation site have already been described. Document WO2005/004727 describes a device for attaching a tape, comprising an ejection barrel for surgical staples, the tape being lodged within the ejection barrel and therefore forming part of the device before use, at the time the device is provided to the surgeon. In the device of WO2005/004727, the tape is unreeled from a first fixation point to a second fixation point by means of a reel housed within the device and on which the tape bears. Nevertheless, a drawback of the device described in WO2005/004727 is that, because the tape is part of the device, the device may be used only for implanting that tape. As a consequence, a new fixation device must be provided for each tape to be implanted. A device for dispensing surgical staples is a complex and sophisticated device, the conception and manufacturing of which require time and money. In addition, another drawback of the device of WO2005/004727 is that, because the tape is lodged within the ejection barrel, it is caused to rub against the inner walls of the barrel and/or against the walls of the staples container, when it is unreeled from a fixation point to the other. This friction undergone by the tape within the confined space of the interior of the barrel may lead to damage the tape and its edges, thereby rendering it traumatic for the body tissues where it is intended to be implanted.

There is therefore a need for a device with which such a tape can be easily and atraumatically fixed, for example at one or both of its ends, in particular in the area of the anterior attachment of the left levator muscle and/or the anterior attachment of the right levator muscle. There is also a need for a universal device, capable of matching any conventional surgical staples dispenser; such a universal device would permit to avoid the manufacture of a staple dispenser for each tape to be implanted. Such a device must be able to be manipulated easily by the surgeon. It must also allow the tape to be fixed, for example, via one of its ends at one location and permit self-adjustment of the tape when the patient is returned to an upright position, or at two different locations, while allowing the surgeon to set the degree of tensioning he wants for the tape when it passes under the urethra.

The present invention responds to this need by proposing a component that can be used in combination with any device for dispensing surgical staples, said component in the first stage making it possible to fix a first end of said tape at a first point of fixation chosen by the surgeon, then to unreel said tape, without damaging it, so as to pass it for example under the urethra while giving it the desired degree of tensioning, and, in a second stage, either to release the second free end of said tape in the contralateral paravesical space or to fix the second end of said tape to a second point of fixation chosen by the surgeon, this being done extremely simply and quickly and in a manner causing little trauma for the patient.

A first aspect of the present invention is a component intended to be mounted on the ejection barrel of a device for dispensing surgical staples, comprising fixing means designed to fix said component on said ejection barrel removably or non-removably, characterized in that it further comprises:

securing means for temporarily securing a surgical tape to said component, said securing means allowing said tape to slide within said component, said securing means comprising at least one slit formed within said component, said slit receiving at least partially said tape, said slit having a longitudinal axis substantially parallel to the longitudinal axis of said ejection barrel when said component is mounted on said ejection barrel.

By virtue of the present invention, it is possible to fix a surgical tape, in particular for suburethral support, in an extremely simple manner, as will become clear from the following description of the implantation method. According to the invention, the tape is able to slide within the component and is therefore able to unreel at the implantation site as desired by the surgeon. Moreover, because the tape slides within a component which is mounted on the ejection barrel of the staples dispenser, i.e., located on the exterior of the ejection barrel, the tape is not in contact with other elements that may be found within an ejection barrel, such as staples container, etc. and that may damage it. Furthermore, on account of the tape being connected to the component by a longitudinal slit authorizing both the temporary securing of the tape to the component and the sliding of the tape therein, the surgeon can, if so desired, confer the desired degree of tensioning on the tape between two points of fixation.

Moreover, because of the orientation of the slit of the component of the invention, the tape is capable of being unreeled parallel to the longitudinal axis of the ejection barrel.

In addition, as will appear from the following description, the component of the invention is adaptable and may be used with any fixation device; thanks to the component of the invention, it is not necessary to manufacture a fixation device for each tape to be implanted.

The component of the invention comprises securing means for temporarily securing the tape to the component, said securing means allowing the tape to slide within said component. By "temporarily securing" is meant in the present application that the securing means allow the tape to be attached to the component at least for a certain time, in particular from the time when the component of the invention is fixed to the ejection barrel of the device for dispensing the surgical staples to the time when the tape is implanted. Moreover, by "securing means allowing the tape to slide within said component" is meant that the tape is slidingly coupled to the component; in other words, the tape is allowed to slide forward and backward, with respect to the longitudinal axis of the ejection barrel on which the component is fixed, within the component. The securing means comprise at least one slit formed within said component, said slit receiving at least partially said tape.

The slit has preferably an elongate shape, said slit having a longitudinal axis substantially parallel to the longitudinal axis of said ejection barrel when said component is mounted on said ejection barrel. The tape is therefore allowed to slide forward and backward, with respect to the longitudinal axis of the slit, within said slit. For example, the dimensions of the slit are designed so that the tape undergoes a gentle friction against the inner walls of the slit, when the tape slides within the slit, for example when the tape is unreeled from the component, as will be explained later.

Said fixing means can be chosen from among clips, hooks, adhesives or screws.

Said component is preferably made of a plastic material.

The ejection barrel can be made of metal or of plastic. The ejection barrel preferably comprises a straight part on which said component is fixed. Thus, in one embodiment of the invention, the component can be fixed on the ejection barrel by friction or interlocking.

Any fixation means allowing one element to be fixed on another, whatever the materials from which these elements are made, can be used in the present invention.

A second aspect of the present invention concerns an assembly comprising a component such as has been described above, characterized in that it additionally comprises a surgical tape, said tape being intended to be received at least partially within said securing means of said component.

Another aspect of the invention relates to a device for dispensing surgical staples, comprising at least one ejection barrel for ejecting said surgical staples, characterized in that it additionally comprises a component or an assembly, as has been described above, mounted on said ejection barrel.

In one embodiment of the invention, said component and said ejection barrel are one and the same element.

Another aspect of the invention is a kit for fixing a surgical tape, characterized in that it comprises:
- at least one device for dispensing surgical staples, comprising at least one ejection barrel for ejecting said staples,
- at least one component such as has been described above, and
- at least one surgical tape.

The present invention further relates to a method for treatment of female stress urinary incontinence, comprising the following steps:
- a) a component of the type described above is made available in which a tape is received, said component being mounted on the ejection barrel of a device for dispensing surgical staples,
- b) a vaginal incision is made under the urethra of the patient to be treated, passing on both sides of the urethra through the peri-urethral fascia, urethropelvic ligament and pelvic aponeurosis, finally reaching the paravesical fossa, thereby defining two paths, namely a right-hand path and a left-hand path, from the vaginal incision to the right-hand or left-hand paravesical fossa,
- c) the distal end of the ejection barrel is introduced in the direction of the right or left levator muscle,
- d) the distal end of the ejection barrel is introduced in the right-hand path or left-hand path until it comes into contact with the anterior attachment of the right or left levator muscle or with the right or left obturator muscle,
- e) a first end of the tape is fixed in the area of the right levator or obturator muscle while triggering ejection of a first staple,
- f) the ejection barrel is drawn back in the proximal direction, and it is then passed under the urethra, while unreeling the tape, which slides in the component,
- g) the distal end of the ejection barrel is introduced in the left-hand or right-hand path until it comes into contact with the anterior attachment of the left or right levator muscle, while unreeling the tape within the left or right paravesical fossa, said tape sliding in the component,
- h) the free end of the tape is released in the paravesical fossa,
- i) the ejection barrel is withdrawn, and the tape is cut before closing the vaginal incision.

According to such a method, the second end of the tape is released without particular fixation in the paravesical fossa, and the tensioning of the tape adjusts automatically (self-adjustment) when the patient assumes an upright position. The second end of the tape, not fixed, attaches itself in the tissues, on account of the nature of the tape, for example the presence of pores, or a widened shape of this second end.

According to another embodiment of the method according to the invention, step h) above is replaced by step j) in which:
- j) the tape is fixed at a second point of fixation situated in the area of the left or right levator muscle or obturator muscle, while triggering the ejection of a second surgical staple.

Before the step of triggering the release of the second staple, it is possible to adjust the tensioning of the tape by sliding it within the component, by means of pulling on its proximal end that protrudes in the proximal direction from the component.

Figure 4:
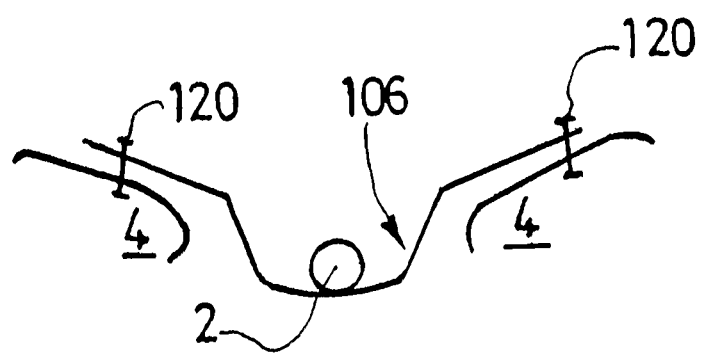
Figure 5:
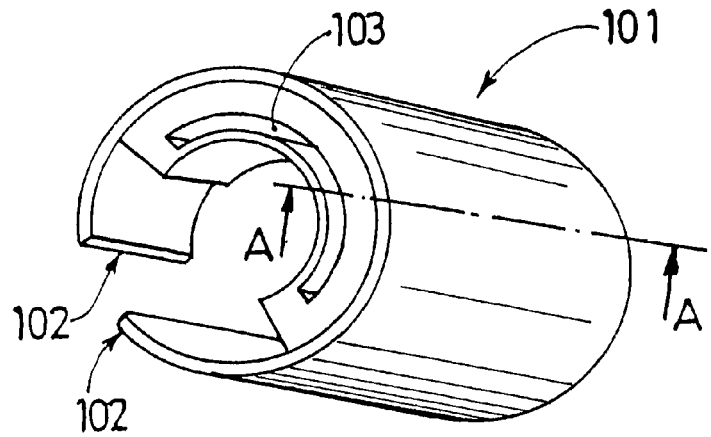
Figure 6:
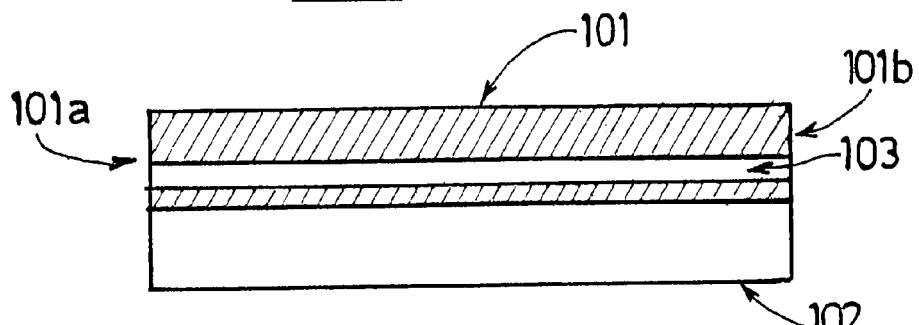
Figure 7:
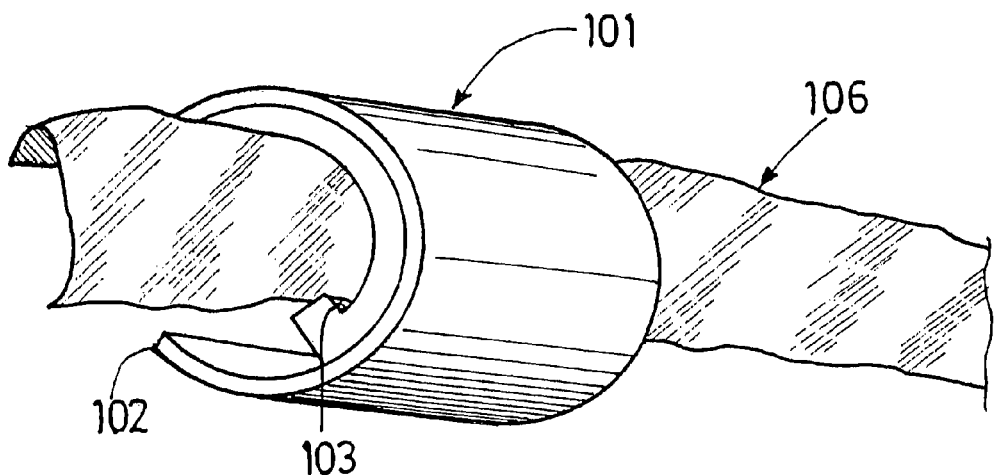
Figure 8:
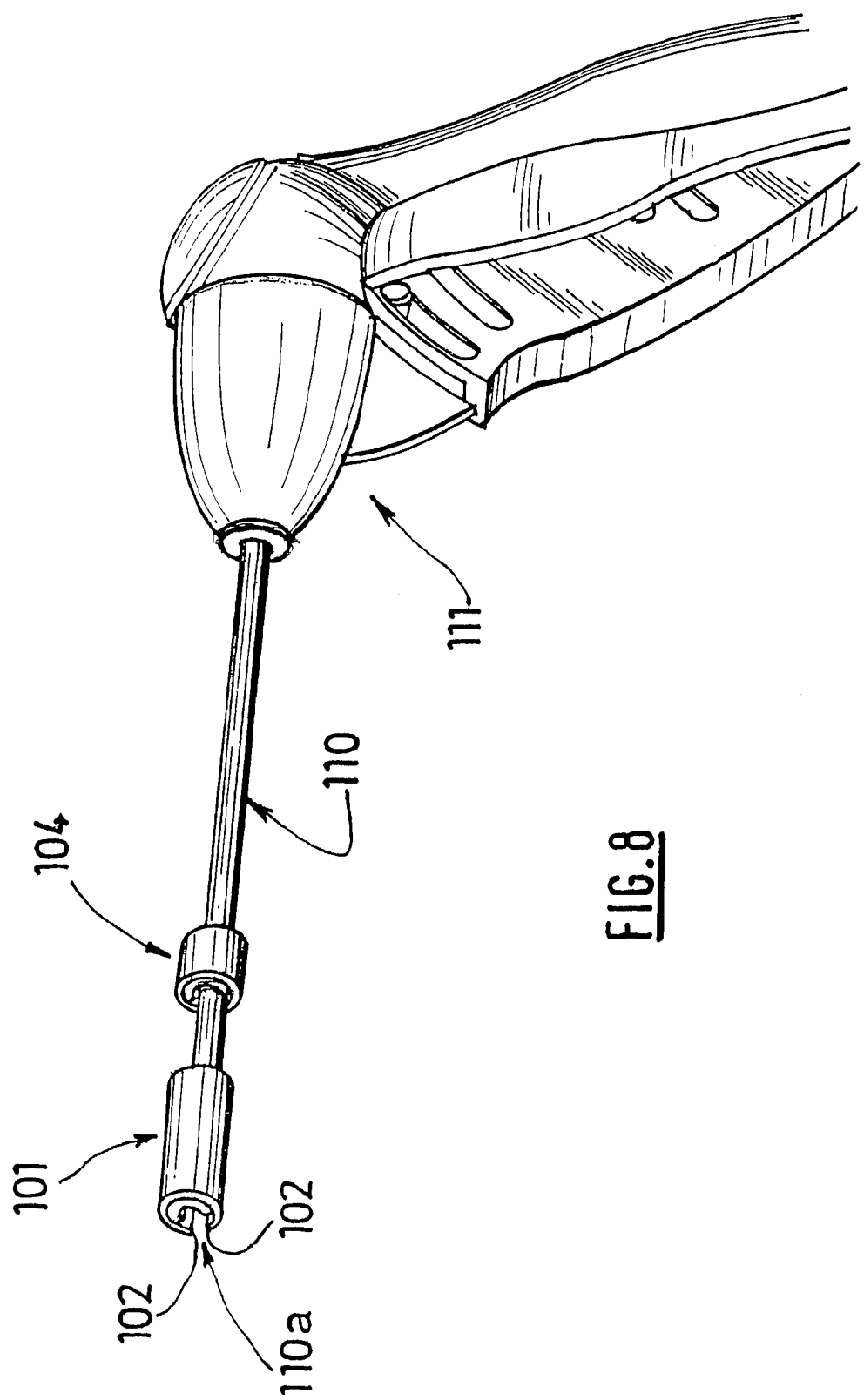
Figure 9:
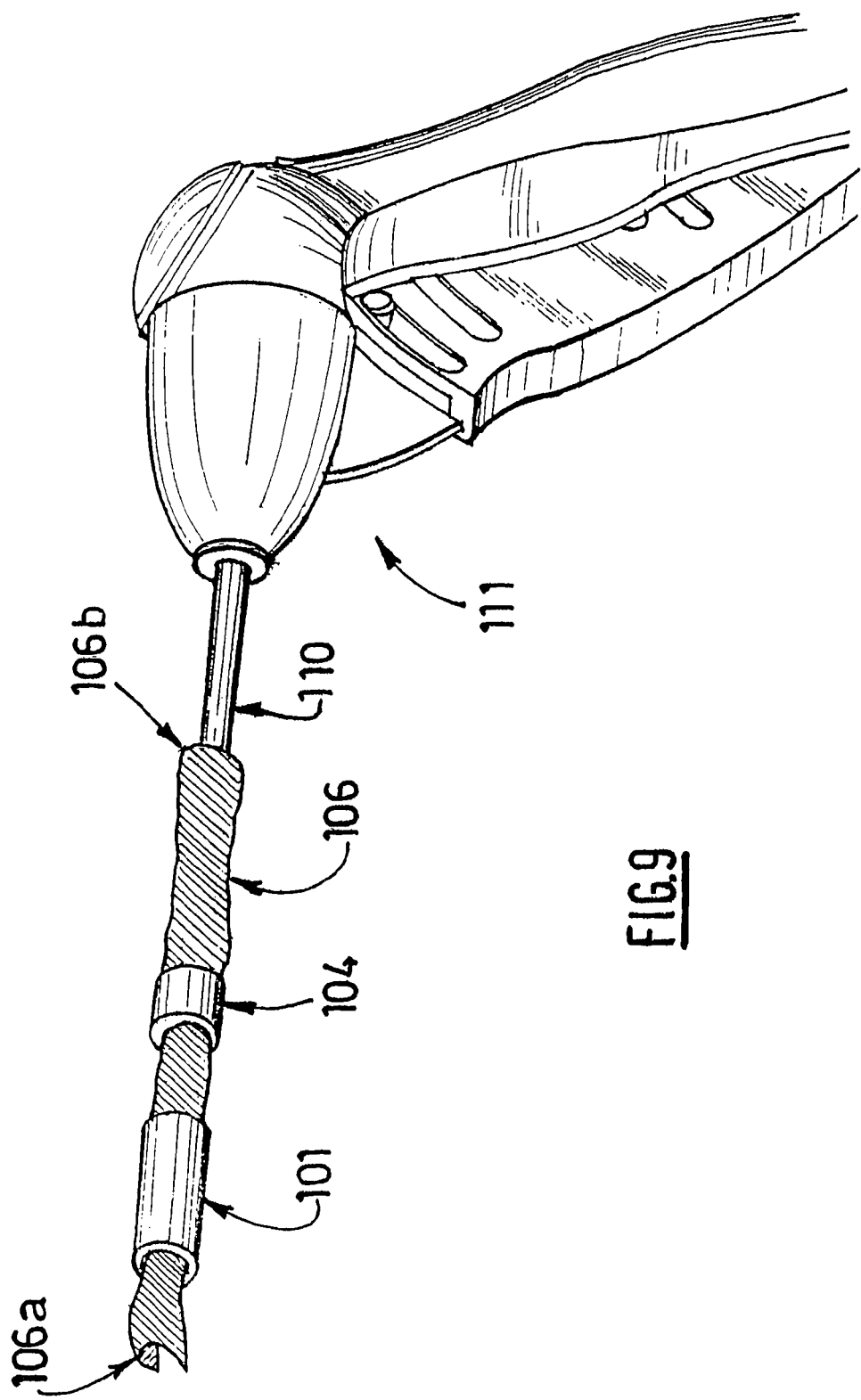
Figure 10:
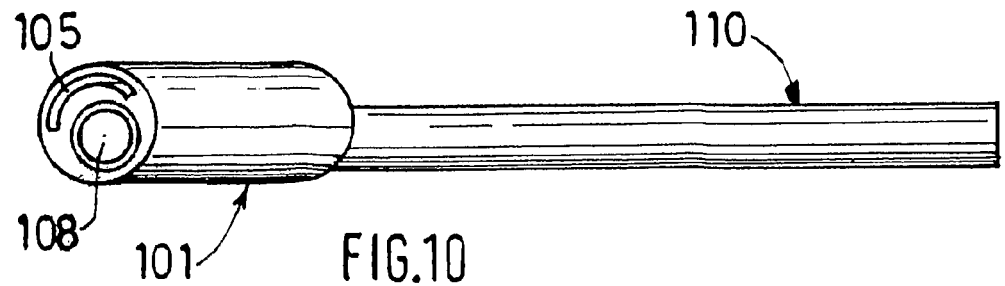
Figure 11:
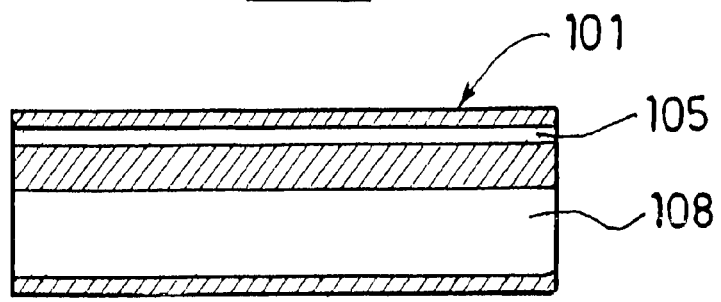

The advantages of the present invention will become clearer from the following description and from the attached drawings, in which:

FIG. 1 is a partial perspective view of a woman's pelvis, showing a tape that has been fitted in place by the retropubic access route, FIG. 2 is a partial perspective view of a woman's pelvis, showing a tape that has been fitted in place by the transobturator access route, FIG. 3 is a partial perspective view of a woman's pelvis, showing a tape that can be fitted in place using a staple-dispensing device according to the invention, FIG. 4 is a schematic side view of a tape that has been fitted in place using a staple-dispensing device according to the invention, when the patient is standing up, FIG. 5 is a perspective view of a component according to the invention, FIG. 6 is a cross-sectional view of the component according to FIG. 5 along the line AA in FIG. 5, FIG. 7 is a perspective view of the component according to claim 5, provided with a surgical tape, FIG. 8 is a perspective view of a staple-dispensing device, on the ejection barrel of which are mounted the component according to FIG. 5 and a second component according to the invention, FIG. 9 is a perspective view of the device according to FIG. 8, provided with a surgical tape, FIG. 10 is a partial perspective view of the ejection barrel of a device for dispensing surgical staples, on which a variant of a component according to the invention is mounted, FIG. 11 is a cross-sectional view of the component according to FIG. 10 along the longitudinal plane passing through the centre of the slit of the component, FIGS. 12 to 15 are perspective schematic views illustrating the method of fixing a surgical tape with the aid of a kit according to the invention in the treatment of female urinary incontinence.

Although, in the present application, the invention is illustrated on the basis of the implantation of a suburethral tape for treatment of female urinary incontinence, any use of the invention in any other field in which it is necessary to implant a tape, and fix it at a fixation point or at several successive fixation points, is envisaged.

FIGS. 5 and 6 show a component 101 according to the invention, intended to be mounted on the ejection barrel 110 of a device 111 for dispensing surgical staples (see FIG. 8), in other words intended to be fixed, temporarily or not, on the outer walls of the ejection barrel 110.

The component 101 shown in FIGS. 5 and 6 is of generally tubular shape, and it comprises fixing means designed to fix said component 101 on the ejection barrel 110 of a device 111 for dispensing surgical staples. In the example shown, the ejection barrel 110 is itself of tubular shape, and the fixing means of the component 101 in FIGS. 5 and 6 are in the form of two clips 102 intended to engage round the ejection barrel 110 and fix the component 101 on the ejection barrel 110 with a snap fit.

In one embodiment (not shown) of the invention, the fixing means could be in the form of hooks or else in the form of an adhesive that affixes the component 101 on the ejection barrel 110. Likewise, in one embodiment (not shown) of the invention, the component 101 has a parallelepipedal shape, for example, and is mounted on the ejection barrel with the aid of claws enclosing, or screwed onto, the ejection barrel 110. Likewise, the ejection barrel itself could have a shape other than tubular, for example a parallelepipedal shape. The ejection barrel preferably comprises a straight part on which the component 101 is fixed.

The fixing means can fix the component 101 on the ejection barrel 110 removably or non-removably.

The component 101 in FIGS. 5 and 6 additionally comprises means for securing a surgical tape 106 (see FIG. 7) to said component 101, these means allowing the tape 106 to slide within the component 101. In FIGS. 5 and 6, these securing means are in the form of a slit 103, having an elongate shape, and formed longitudinally in the body of the component 101 and extending along the full length of the component 101. The slit 103 thus opens out at the two ends, namely the distal end 101a and the proximal end 101b, of the component 101, as is shown in FIG. 6.

In the context of the present application, "the distal end" of an element or of a device is an expression designating the end farthest away from the user's hand, while "the proximal end" is an expression designating the end nearest to the user's hand. Likewise, in the context of this application, "the distal direction" is an expression designating the direction of ejection of a staple, while "the proximal direction" is an expression designating the direction opposite to the direction of ejection.

The slit 103 is intended to receive a surgical tape 106, as shown in FIG. 7. Preferably, the longitudinal slit 103 is dimensioned to allow the surgical tape 106 to slide with slight friction, such that said tape 106 remains connected to the component 101 unless too great a traction is exerted on it. Thus, while the surgeon is manipulating the assembly composed of component and tape prior to implantation, the tape 106 remains connected to the component 101. Anyway, because the friction exerted on the tape 106 when it slides within the slit 103 is very slight, the tape 106 is not damaged.

The length of the component 101 and the dimensions, namely the length and width, of the slit 103 are suitable for keeping the tape 106 connected to the component 101 and near to the ejection barrel 110 during the time that the surgeon manipulates the staple-dispensing device until a first end of the tape 106 is fixed in the tissues upon its implantation. During these steps, and the subsequent steps, and in particular during the optional step of fixing the tape at least one second fixation point, the tape is allowed to slide within the slit 103 in the distal direction and/or in the proximal direction.

For example, for a surgical tape 106 with a length of approximately 150 mm, it is possible to use a component 101 according to the invention with a length of approximately 35 mm.

In one embodiment of the invention (see FIG. 8), it is possible to mount a second component 104 according to the invention on the ejection barrel 110, at a distance from said component 101, in order to keep the tape 106 near to the ejection barrel 110 at a second location on the ejection barrel 110. Such a second component 104 then acts as a guide. Alternatively, it is possible to mount on the ejection barrel 110 a single component 101 whose length is slightly smaller than the length of the ejection barrel 110.

The surgical tape intended to be used in combination with the component 101 of the invention can be any tape used in surgery: this tape is preferably made of a compatible and flexible material. This tape can be in the form of a textile or non-textile, can be made of synthetic or non-synthetic material, or can be made of absorbable or non-absorbable material. It preferably has an elongate rectangular shape so as to be able to slide within the longitudinal slit 103 in the distal direction and in the proximal direction. Such a tape can, for example, have a length of from 80 mm, in the case where the tape is fixed only at one point and self-adjusts naturally, to approximately 150 mm, for example, in the case where the tape is intended to be fixed at two points.

Tapes suitable for the present invention are described, for example, in the following documents: WO02/28312 and WO03/096928.

FIG. 8 shows the component 101 from FIGS. 5 and 6 mounted on the ejection barrel 110 of a device 111 for dispensing staples (not shown). The staple-dispensing device suitable for the present invention can be any dispensing device, such as a stapler or a dispenser equipped with a staple-ejecting barrel; the staples intended to be used to fix the tape 106 are preferably stored within the ejection barrel 110.

Devices used for dispensing surgical staples and suitable for the present invention are described, for example, in the following documents: WO03/075773 and WO2006/037893.

FIG. 8 shows a device 111 for dispensing surgical staples in which the ejection barrel 110 has a tubular or cylindrical shape. Thus, the component 101 from FIG. 5 has been mounted near the distal end 110a of the ejection barrel 110 of the device 111 in FIG. 8 by snap-fitting it in place with the aid of the two clips 102. The clips 102 hold the component 101 on the ejection barrel 110 fixedly, and preferably without any possibility of sliding of said component 101 on the ejection barrel 110.

FIG. 8 also shows a second component 104 according to the invention, also mounted on the ejection barrel 110 in the proximal direction from the component 101; this second component 104 has a different length than the first component 101 in the example shown and comprises a slit 103 identical to that of the component 101. In another embodiment (not shown) of the invention, the length of this second component is identical to that of the first component 101. This second component 104 is intended also to receive the tape 106 and has the function of a guide, as will be explained below. In one embodiment of the invention, this second component 104 is not present or is connected to the first component 101.

FIG. 9 shows the staple-dispensing device 111 from FIG. 8 equipped with the components 101 and 104 within whose slits 103 a tape 106 has been passed. The tape 106 is able to slide within the slits 103 of the two components 101 and 104 in the distal direction or in the proximal direction, ie parallel to the respective longitudinal axis of the ejection barrel 110 and of the slit 103, under the effect of a traction exerted for example by the surgeon on one of the ends, namely distal end 106a or proximal end 106b, of the tape 106.

FIG. 10 shows a variant of the component 101 from FIG. 5, mounted on the ejection barrel 110 of a device (not shown) for dispensing surgical staples.

The component 101 in FIG. 10 is formed by a solid cylinder within which there is a first cylindrical lumen 108, the longitudinal axis of said cylindrical lumen being off-centre in relation to the longitudinal axis of the solid cylinder. This cylindrical lumen is intended to receive the ejection barrel 110, as shown in FIG. 10, said ejection barrel 110 and said component 101 being fixed to each other by interlocking and by friction or adhesive bonding. The solid cylinder also comprises a longitudinal slit 105, similar to the slit 103 described for the component 101 in FIG. 5, and intended to receive a surgical tape 106 (not shown).

The method of fixing a surgical tape will now be described with reference to FIGS. 12 to 15.

Once the surgeon has chosen a tape 106 to be implanted and has chosen the staple-dispensing device 111 that he wishes to use, he selects a component 101 according to the invention suitable for the ejection barrel 110 of the staple-dispensing device in question. He fixes the component 101 on the ejection barrel 110 by snap-fit engagement, by interlocking engagement, or by any other suitable means. Alternatively, the component 101 can be supplied already fitted on the ejection barrel 110, or the component 101 can form part of the ejection barrel 110 of the device 111 for dispensing staples, the component 101 being located exteriorly of the ejection barrel 110.

The surgeon then takes the tape 106 to be implanted and passes it through the slit 103 of the component 101 and, if necessary, through the slit 103 of a second component 104 also mounted on the ejection barrel 110 of the dispensing device 111. Alternatively, the tape can be supplied already fitted on the component 101 and/or on the component 104.

The surgeon then adjusts the tape 106 by sliding it in the slit or slits 103 of the component or components 101, 104 such that the distal end 106a of the tape 106 protrudes slightly from the distal end 110a of the ejection barrel 110. The dimensions of the slit 103 allow the tape 106 to slide within said slit 103 with soft friction, so that the tape 106 is not damaged by said friction.

The surgeon then makes a vaginal incision below the urethra of the patient to be treated, passing through the peri-urethral fascia, the urethropelvic ligament and the pelvic aponeurosis, finally reaching the paravesical fossa, thereby defining two paths, namely a right-hand path and a left-hand path, from the vaginal incision to the right-hand or left-hand paravesical fossa.

Figure 12:
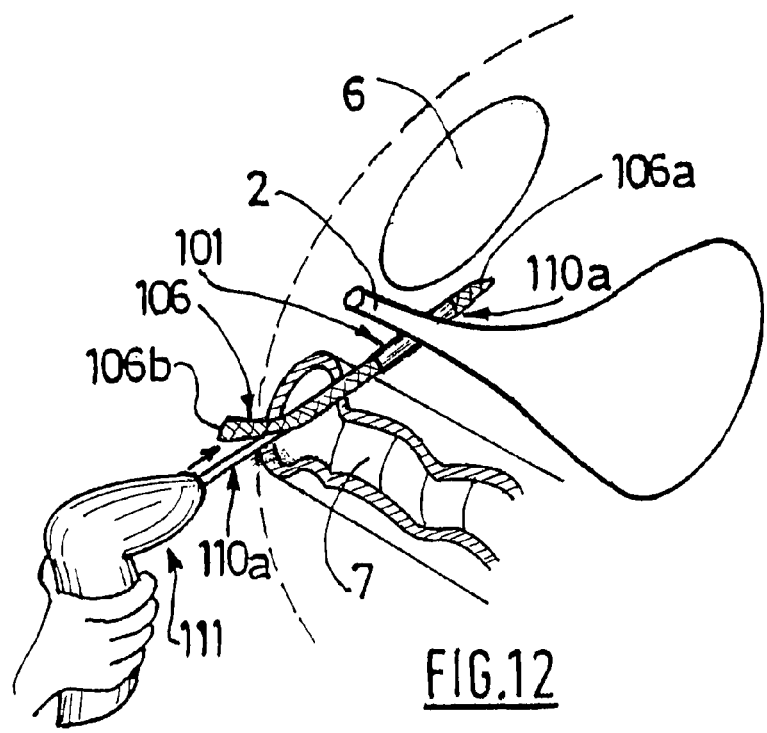

The surgeon introduces the distal end 110a of the ejection barrel 110 into the right-hand path in the direction of the right levator muscle or right obturator muscle, for example, as shown in FIG. 12.

As the distal end 110a of the ejection barrel 110 passes through the tissues, the distal end 106a of the tape 106 is preferably folded back on the distal end 110a of the ejection barrel 110. This is possible because the tape 106 is unreeled from the slit 103 parallel to the longitudinal axis of the ejection barrel 110.

Thus, when the distal end 110a of the ejection barrel 110 comes into contact with the right levator or right obturator muscle, the surgeon triggers the ejection of a surgical staple 120 (see FIG. 13) which will fix the distal end 106a of the tape 106, which was folded back in front of the distal end 110a of the ejection barrel 110, on the right levator or right obturator muscle.

Figure 13:
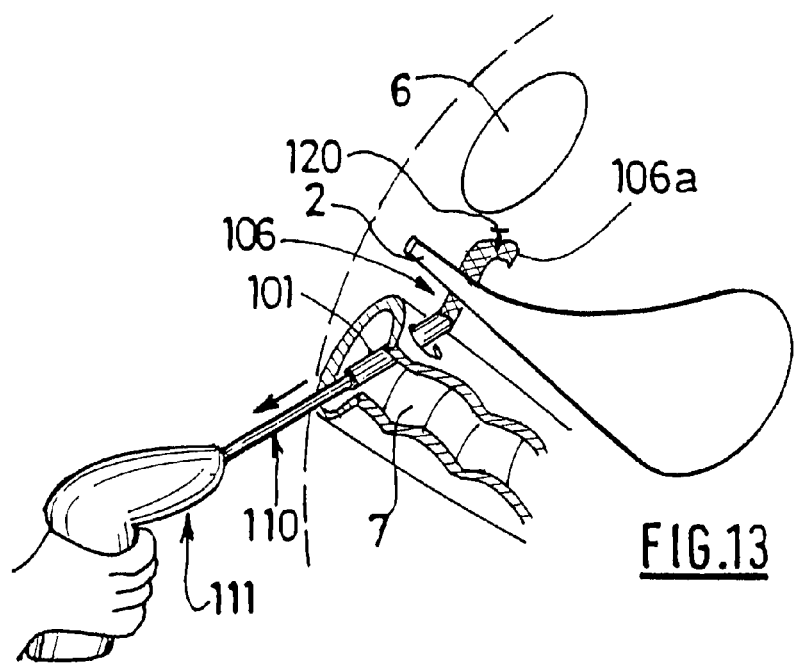

The surgeon then draws the ejection barrel 110 slightly back in the proximal direction, as shown in FIG. 13.

With the distal end 106a of the tape 106 now fixed to the right levator or obturator muscle by way of a first surgical staple 120, the tape 106 slides within the slit 103 of the component 101, and optionally of the component 104, mounted on the ejection barrel 110, in line with the surgeon moving the ejection barrel 110.

The surgeon then loops round the urethra 2 with the ejection barrel 110, by moving the distal end 110a of the ejection barrel 110 under the urethra. If necessary, during this operation, the surgeon can make use of a spatula (not shown) in the shape of a trough which he places between the urethra and the tape 106 for the purpose of both protecting the urethra and of creating a space between the urethra and the tape in order to facilitate the subsequent adjustment of the tensioning of the tape 106. In doing so, he unreels the tape 106, which itself passes under the urethra, and then once again moves the ejection barrel 110 in the distal direction, this time along the left-hand path in the direction of the left levator or obturator muscle.

If the method involving self-adjustment of the tape has been chosen, the surgeon then releases the proximal end 106b of the tape in the left obturator foramen. He cuts the second end of the tape 106 and closes the vaginal incision. The tape self-adjusts when the patient resumes an upright position.

Figure 14:
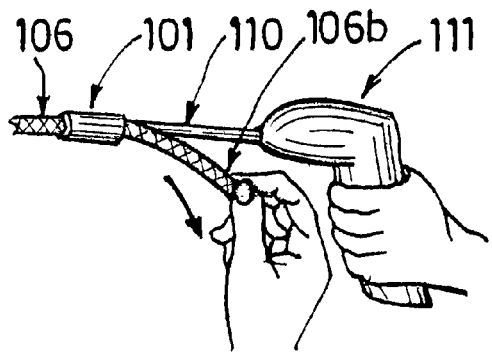

If the method involving fixing the tape at two points has been chosen, then, when the ejection barrel 110 is pointed in the direction of the left levator or obturator muscle, the surgeon can adjust the tensioning of the tape 106 by gripping it, for example using his fingers or another gripping instrument, at the proximal end 106b of the tape 106 protruding proximally from the component or components 101, 104 mounted on the ejection barrel 110, as is shown in FIG. 14.

When the tensioning of the tape 106 is adjusted and the distal end 110a of the ejection barrel 110 is in contact with the left levator or obturator muscle, the surgeon triggers the ejection of a second surgical staple 120, which will fix the tape 106 in the area of the left levator or obturator muscle.

The surgeon then simply has to draw the ejection barrel 110 back in the proximal direction. During this manoeuvre, the tape 106 continues to unreel by sliding through the slits 103 of the components 101 and, optionally, 104. The surgeon then cuts the tape 106 at a point located proximally from the second point of fixation and closes the vaginal incision.

Figure 15:
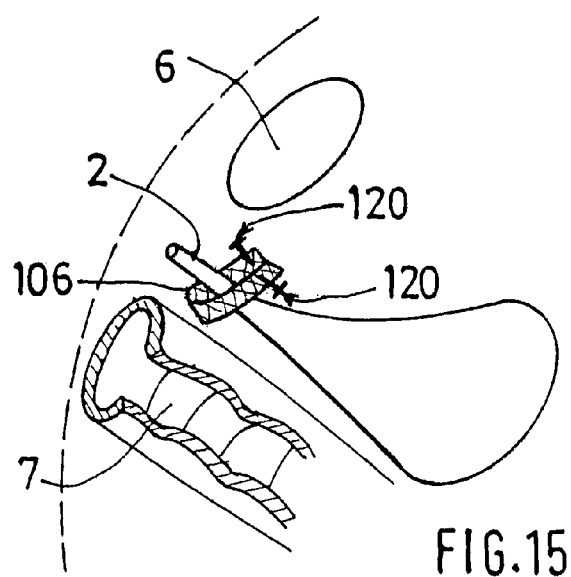

According to this second method, the tape 106 is thus fixed on both sides of the urethra, as is shown in FIGS. 4 and 15. As is clear from these figures, the path followed by the tape 106 is particularly short and causes little trauma for the patient.

The method according to the invention for fixing and/or implanting a suburethral tape is particularly simple and quick and causes little trauma for the patient.

The invention claimed is:

1. A method for treatment of female stress urinary incontinence, the method comprising:
   a) providing a component in which a tape is received, the component including a lumen for receiving an ejection barrel therein, the lumen defining a first longitudinal axis, the component being mounted on a distal end of an ejection barrel of a device for dispensing surgical staples, wherein the component comprises a fixing means for removably mounting the component on the ejection barrel, and a slit for temporarily securing the tape to the component, the slit defining a second longitudinal axis which is substantially parallel to the first longitudinal axis, the slit receiving the tape at a proximal end of the component, discharging the tape at a distal end of the component, and allowing the tape to slide therethrough along a full length of the component;
   b) making a vaginal incision under an urethra of a patient to be treated, creating a path on both sides of the urethra through peri-urethral fascia, urethropelvic ligament and pelvic aponeurosis, finally reaching paravesical fossa, thereby defining a right-hand path and a left-hand path, from the vaginal incision to a right-hand or left-hand paravesical fossa;
   c) introducing the distal end of the ejection barrel in the right-hand path or left-hand path until it comes into contact with an anterior attachment of a right levator muscle or a right obturator muscle if introduced in the right-hand path, or a left levator muscle or a left obturator muscle if introduced in the left-hand path;
   d) fixing a first end of the tape in an area of the contacted right or left levator or obturator muscle of step c) while triggering ejection of a first staple;
   e) drawing back the ejection barrel in a proximal direction, and then passing under the urethra, while unreeling the tape, which slides in the component;
   f) introducing the distal end of the ejection barrel in the other of the left-hand or right-hand path of step c) until it comes into contact with the anterior attachment of the right levator muscle or the right obturator muscle if introduced in the right-hand path, or the left levator muscle or the left obturator muscle if introduced in the left-hand path, while unreeling the tape within the paravesical fossa, the tape sliding in the component;

g) releasing a second end of the tape in the paravesical fossa;

h) withdrawing the ejection barrel; and i) closing the vaginal incision.

2. A method according to claim 1, wherein step g) further comprises fixing the second end of the tape at a second point of fixation situated in the area of the contacted left or right levator or obturator muscle of step f), while triggering the ejection of a second surgical staple.

3. A device for dispensing surgical staples comprising at least one ejection barrel for ejecting surgical staples, a first component mounted on the at least one ejection barrel, the first component including a body having a proximal end and a distal end, a lumen defined within the body and extending through the proximal and distal ends of the body for receiving the at least one ejection barrel therein, the lumen defining a first longitudinal axis, fixing means for removably or non-removably fixing the component on the at least one ejection barrel; and, a slit formed within the body of the first component and extending along a full length of the first component through the proximal and distal ends of the body, the slit defining a second longitudinal axis parallel to the first longitudinal axis and having an elongated cross-section orthogonal to the second longitudinal axis, the slit configured to receive tape at the proximal end of the body, the slit configured to discharge tape at the distal end of the body, and the slit allowing tape to slide therethrough along the full length of the body, and, a second component mounted on the at least one ejection barrel at a distance from the first component, the second component including a slit formed within the second component and extending along a full length of the second component, the slit of the second component coincident with the second longitudinal axis of the slit of the first component, the slit of the second component configured to receive tape and to allow tape to slide therethrough.

4. A device according to claim 3 wherein the device is a surgical stapler and the ejection barrel is a distal end of the surgical stapler.

5. A device according to claim 3 wherein the slit of the second component has an elongated cross-section orthogonal to the second longitudinal axis.

6. A device according to claim 3, wherein the fixing means is chosen from among clips, hooks, adhesives or screws.

7. A device according to claim 3, wherein at least one of the first and second components is made of a plastic material.

8. A device according to claim 3, further comprising a surgical tape, the surgical tape being dimensioned and configured to be received at least partially within the slit of the first component and the slit of the second component.

9. A device according to claim 1, wherein the slit of the first component is arcuate in shape along the full length of the component.

10. A device according to claim 1, wherein the slit of the second component is arcuate in shape along the full length of the component.

11. A device according to claim 3, wherein the body of the first component is cylindrical.

12. A device according claim 3, wherein the first component and the ejection barrel are a unitary element.

* * * * *